United States Patent

Samimi

Patent Number: 6,059,801
Date of Patent: *May 9, 2000

[54] BLADDER SAVER RETROPUBIC LIGATURE CARRIER DEVICE

[76] Inventor: Darius Samimi, 11180 Warner Ave., Suite 165, Fountain Valley, Calif. 92708

[ * ] Notice: This patent issued on a continued prosecution application filed under 37 CFR 1.53(d), and is subject to the twenty year patent term provisions of 35 U.S.C. 154(a)(2).

[21] Appl. No.: 09/046,614

[22] Filed: Mar. 24, 1998

Related U.S. Application Data

[60] Provisional application No. 60/035,603, Mar. 24, 1997.

[51] Int. Cl.[7] .................................................... A61B 17/04
[52] U.S. Cl. ............................................................ 606/148
[58] Field of Search .................................... 604/174, 177; 606/148

[56] References Cited

U.S. PATENT DOCUMENTS

| | | | |
|---|---|---|---|
| 5,391,156 | 2/1995 | Hildwein et al. | 604/174 |
| 5,637,112 | 6/1997 | Moore et al. | 606/148 |
| 5,685,857 | 11/1997 | Negus et al. | 604/170 |
| 5,728,103 | 3/1998 | Picha et al. | 606/108 |
| 5,814,021 | 9/1998 | Balbierz | 604/174 |
| 5,817,062 | 10/1998 | Flom et al. | 604/174 |

*Primary Examiner*—Gary Jackson
*Assistant Examiner*—Duphna Shai

[57] ABSTRACT

A bladder saver retropubic ligature carrier device consisting of a stand and a modified trocar. The stand has a removable stylet which is disposed at approximately a 20 degree angle from a planar anterior surface of a cubical, conically configured base member. The stylet a posteriorly joined pair of rods, and it can be replaced with a modified trocar having a spiral tip and striated handle. The modified trocar, used in combination with the stand can be guided by a physician to gently and accurately enter bodily tissue.

9 Claims, 2 Drawing Sheets

BLADDER SAVER RETROPUBIC LIGATURE CARRIER DEVICE

Priority is claimed to Provisional Patent Application Ser. No. 60/035,603 filed on Mar. 24, 1997, the disclosure of which is herein incorporated by reference.

FIELD OF THE INVENTION

The present invention relates generally to surgery apparatuses which a physician utilizes to actuate an operation through bodily tissues, especially ir tie treatment of female urinary incontinence.

More specifically, the present invention is directed to such a bladder saver retropubic ligature carrier device having a stand or base and a needle with a specially designed handle and contoured tip. The bladder saver retropubic ligature carrier device is compact, easily adaptable to a variety of surgical procedures, and represents a cutting-edge surgical tool capable of being used in traditional as well as newly pioneered operations for treating female urinary incontinence disorders.

BACKGROUND OF THE INVENTION

Treatment of female urinary incontinence has been attempted by various methods and devices throughout the decades. Generally, physicians have endeavored to exercise various puncture techniques wherein the wall of the vagina is undesirably disturbed and damaged.

Typically, female urinary incontinence is remedied with tying the urethro-vesical junction to the back of the symphysis pubis. With existing surgical devices, physicians have had few options to conduct alternative medical procedures. Moreover, traditional medical procedures have always involved application of general anesthesia because of the invasive nature of the remedial action.

One of the most famous treatments for female urinary incontinence is the Perayra technique. The original Pereyra technique used No. 30 stainless wire, which was looped through the vagina without a vaginal incision, by the blind passage of a specially designed needle through a suprapubic incision.

In the modified Pereyra procedure, the superior wall of the vagina is sutured to the abdominal wall rather than structured in the retropubic region. The modified Pereyra procedure involves the use of a ligature carrier having a brace to guide a retractable needle for extension and retraction. The trace includes a generally flat serrated or striated brace handle from which parallel guides extend back, away from the needle tip. The needle's end is angulated and has an eye at its tip. The needle slides through a hole in the brace handle. As has been recounted in prior art of record, there exist numerous explanations for high failure rates of the Pereyra procedure.

In another treatment, the Burch Procedure, the vaginal fascia used to elevate the urethro-vesical angle and the vaginal fascia near the urethra are sutured to Cooper's ligament, ilecpectineal ligament after dissection in retzius space.

Endoscopic suspension was first described in 1973 by Stamey. The innovation was to emphasize the use of the cystoscope to control accurate placement of the suspending sutures in his technique. A T-shaped vaginal incision is made in the anterior vaginal wall and the periurethral tissue exposed. Then, through a short suprapubic incision, the specially designed Stamey needle is introduced through the rectus fascia with the needle in place. Cystoscopic inspection is performed with movement of the needle. Small dacron buttresses are used to prevent suture pull through. Dacron tubes are used to buttress the endopelvic fascia.

Gitte and Laughlin, in 1988, modified the Stamey procedure by making no vaginal incision at all. Instead, they allow the monofilament nylon suture through the vaginal epithelium. In this technique, permanent sutures are withdrawn by a long suspension needle retropubically to the stab incision, where they are secured to fat. It is suggested that over time, the sutures pull through the subcutaneous tissues and then become attached to the rectus fascia with appropriate tension. Vaginal repithelization occurs over these sutures.

None of the previous tools, in combination with any of the aforementioned techniques for treating female urinary incontinence, has been suitable for conducting a procedure which can be performed without an incision on the vaginal wall. Furthermore, none of such tools, in combination with any procedures, has featured an absence of anchoring of the bladder neck suspension and suture to the anterior rectus fascia.

In a new approach, to avert postoperative pain syndrome due to nerve entrapment, the present invention is utilized to anchor the bladder neck with suspending sutures to the edge of pubic bone on the scarpa fascia and rectus abdominus tendinous plus Cooper ligament. It is recognized that the present invention has been specially adapted to serve as a necessary apparatus for successfully performing the new procedure. As a result of employing the present invention in combination with the new procedure, a surgeon should expect patients to exhibit increased support and remarkable scarification after operations.

To understand the setting in which the present invention functions, the new operation procedure is herein described for reference. First, a special long suspension needle is passed through the anterior scarpa fascia, then the rectus tendinous abdominus and the Cooper ligament, toward the undersurface of the symphysis pubis, the retropubic fat pad and the endopelvic fascia and the vaginal wall into the vagina, lateral to the urethrovesical junction, under direct finder guidance. A No. 2 monofilament nylon suture is threaded through the needle's eye, withdrawn to the suprapubic port, and tagged with a hemostat clamp.

Next, the vaginal side tail of the nylon suture is loaded with a Mayo or curve needle. The suture is placed in a circular or spiral fashion incorporating full thickness in the vaginal wall 1–1.5 cm on the lateral side of the urethrovesical level. The suture end is replaced on the long needle eye and withdrawn through the second puncture on the junction of the scarpa fascia and the edge of the symphysis pubis, 1 cm from the first puncture and tagged with hemostat.

In this technique, no vaginal incision is necessary because the suture buries itself by gradually penetrating through the vaginal epithelium and then making remarkable scarification on the endopelvic ligament and the retropubic structure, plus on the rectus abdominus tendinous, the Cooper ligament, and the scarpa fascia on the edge of the pubic bone under subcutaneous fat. At the time treat the surgeon passes the suspension needle through the lateral edges of the incision, he leaves a bridge of the scarpa fascia, the rectus abdominus tendinous, and the Cooper ligament, between the suspending sutures, for suspension at the end of cystoscopy. The cystoscopy is performed to help assure that there has been no injury to the bladder.

The rigid cystoscopy assists in confirming that adequate support has been given to the urethra and bladder neck. If the suspension sutures have unintentionally penetrated the bladder wall, such a case is noticed at the time so the cystoscopy and suture can be pulled out and the operation can be repeated. Also, the lateral aspect or 3, 9 o'clock of the urethrovesical junction and the lower bladder must be seen clearly with no oozing or bleeding and no suture violation. If there is suture violation, the surgeon can pull it cut and re-attempt correct placement. The suprapubic catheter with memory must be placed under the supervision of the cystoscopy surgeon. The catheter must be fixed with several sutures for prevention of dislodging or extravasation. Care must be taken to ensure that the catheter functions satisfactorily.

The monofilament sutures are tied over a reinforced 1–1.5 cm scarpa fascia and the rectus abdominus tendinous attached to the pubic tone. After pushing or bringing the urethrovesical junction to the retropubic space or normal position, moderate tension is required to furnish the support necessary to treat urinary stress incontinence.

In short, a surgeon utilizing the present invention restores the anatomical and physiological position of the proximal urethra, in such a fashion, as to allow transmission of intra-abdominal pressure. Urethral closure pressure is enhanced at least to the same degree and sometimes to a greater degree than normal.

Accordingly, the need arises for a bladder saver retropubic ligature carrier device with a specially designed tip and main body, which allows a physician to exercise increased dexterity and achieve greater operation success.

SUMMARY OF THE INVENTION

By the present invention, a bladder saver retropubic ligature carrier device or the carrying cut procedures to treat female urinary incontinence is disclosed. The present invention includes a double-pronged stand and a special trocar.

Accordingly, one of the objects of the present invention is to provide a bladder saver retropubic ligature carrier device for reducing the duration of operation procedures by up to 53 percent, while preventing bladder violation.

Another of the objects of the present invention is to provide a bladder saver retropubic ligature carrier device which is capable of granting the surgeon increased dexterity and greater surgical accuracy.

Yet another of the objects of the present invention is to provide a bladder saver retropubic ligature carrier device which is capable of facilitating the operation's sling procedure.

Still another of the objects of the present invention is to provide a bladder saver retropubic ligature carrier device which provides overall better operational results because less repeat procedures are required.

A further object of the present invention is to provide bladder saver retropubic ligature carrier device which assists the surgeon in maintaining low morbidity and complications.

Another object of the present invention is to provide a bladder saver retropubic ligature carrier device for the purposes described which has a mechanism to avoid needle stick of the surgeon's fingers.

In view of the above-mentioned and other objects, all of which will become more readily understood as the nature of the present invention is better understood, the invention comprises in the novel combination and arrangement of parts hereinafter more fully described, illustrated, and claimed with reference being made to the attached drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention will be seen to relate to bladder saver retropubic ligature carrier device 10 of unique design. The present invention is comprised primarily of a cast metal stand 20 and a modified trocar 30.

The bladder saver retropubic ligature carrier device 10 has a primary purpose of enabling a surgeon to pass through retropubic anatomy (not shown) without posing a danger of bladder (not shown) and vessel injury (not shown). Thus, the stand 20 is designed to serve as a bridge for the trocar 30 during an operation.

Figure 1:
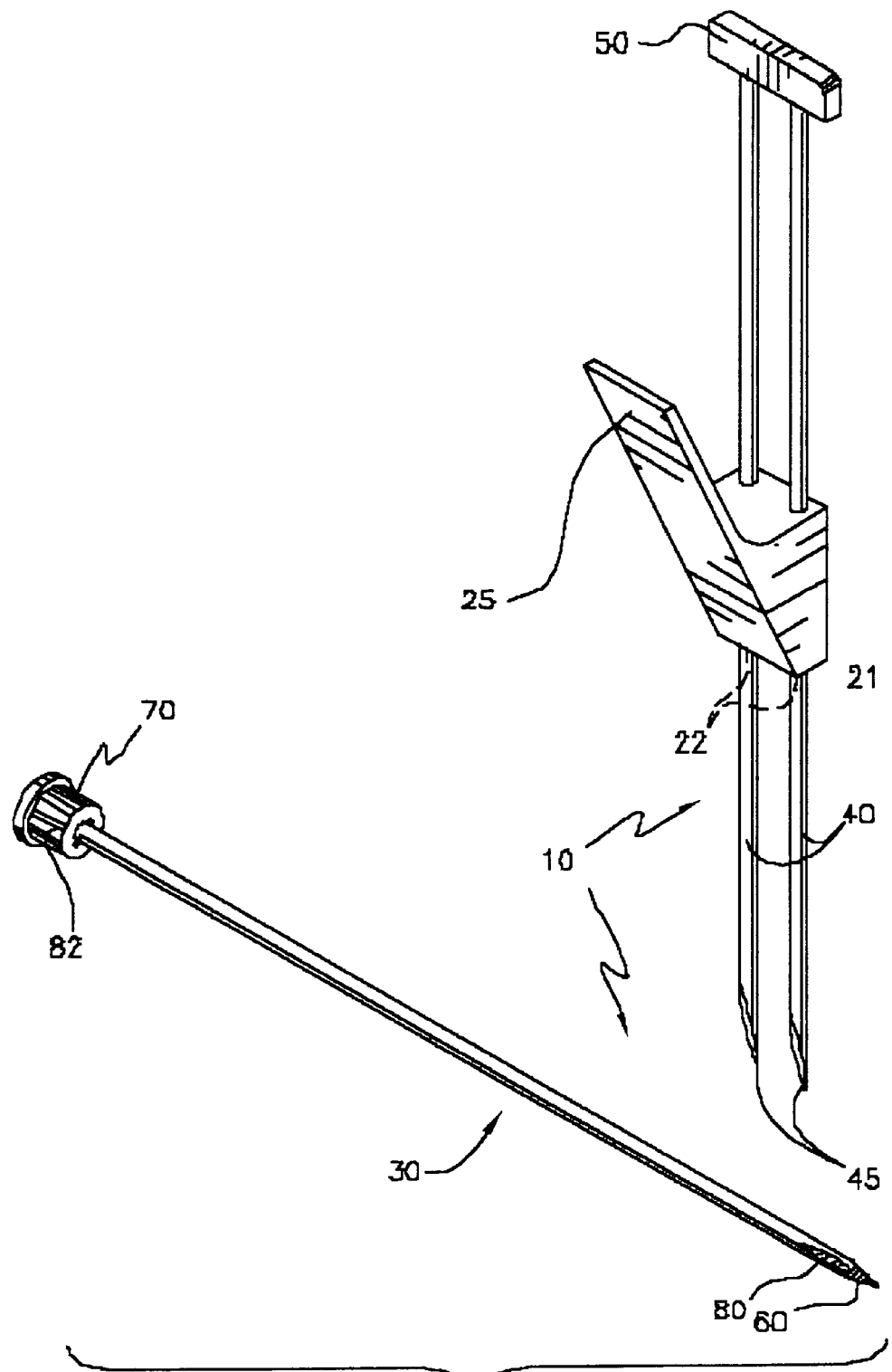
FIG. 1 is an environmental perspective view of the present invention, showing the stand text to the modified trocar.
Figure 2:
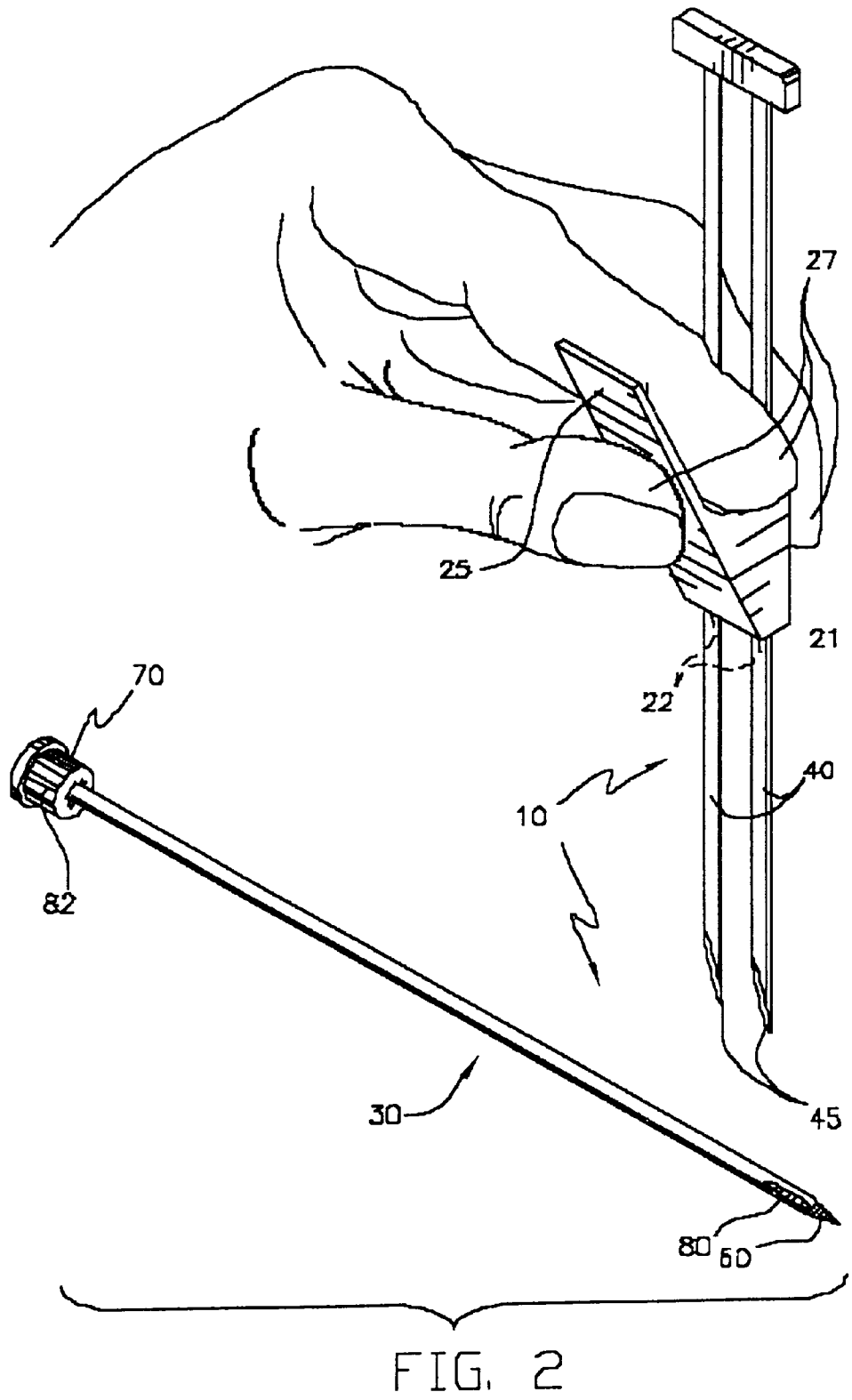
FIG. 2 is an exploded environmental perspective view of the present invention, illustrating one method of handling of the present invention.

In the preferred embodiment of the present invention, as shown in FIG. 1, the stand 20 is composed of a base portion 21 of a cubical conical configuration with an exaggerated planar anterior surface 25. Base portion 21 serves as a holder for the surgeon's fingers 27, as shown in FIG. 2. The surgeon's fingers 27 are placed above and below the planar anterior surface 25 to allow a premium of movement for the stand 20.

Apertures 22 are located in base portion 2, allowing it to communicate with metal rods 40. Depending underneath and through base portion 21, rods 40 also communicate with corresponding apertures (not shown) located on the opposite side of base portion 21. Rods 40 are set parallel to one another and joined together via brace 50 at the posterior end of stand 20. Brace 50 is a fixed connection between rods 40, thus forming a stint or stylet in combination with rods 40. During an operation, the surgeon will find it useful to be able to utilize stylets of various lengths within base portion 21. Metal rods 40 have cutting tips 45 disposed at the anterior ends of stand 20. Each cutting tip 45 resembles a planar stroke made at the end of each metal rod 40.

In short, the stand 20 exhibits planar anterior surface 25 depending at approximately a 20 degree angle from the plane of rods 40. During operation procedures, the surgeon can reliably manipulate the stand 20 by placing fingers 27 above and below planar anterior surface 25 and rods 46.

To further operation procedures, modified trocar 30 may replace rods 40 in base portion 21, such that apertures 22 communicate with modified trocar 30. In this application, modified trocar 30 can be accurately guided inside a patient's body as the surgeon employs stand 20.

Modified trocar 30 pierces through bodily tissue (not shown), with no injury to the bladder (not shown) with spiral tip 60. Resembling a screw head, spiral tip 60 creates a less invasive entrance than a conventional trocar. Unlike a conventional trocar, which has a smooth needle tip (not shown), modified trocar 30 can be twisted as it penetrates bodily tissue so that spiral tip 60 makes a gradual entrance. Modified trocar 30 has an eye 80 located closely behind spiral tip 60 for receiving suture (not shown). In addition, modified trocar 30 has a striated handle 70 which assists the surgeon in maintaining his grip as modified trocar 30 is twisted. Striated handle 70 is of general cylindrical shape with a series or parallel lines 82 running the length of its cylindrical shape for increased dexterity.

In summary, the above described bladder saver retropubic ligature carrier device provides for ease of use and various application, thus providing significant advances in operating technique.

It is to be understood that the present invention is not limited to the sole embodiment described above, but encompasses any and all embodiments within the scope of the disclosure.

I claim:

1. A retropubic ligature carrier apparatus for use with a trocar in actuating an operation through bodily tissues, especially in the treatment of female urinary incontinence, comprising:

a stand, serving as a bridge for the trocar, said stand having an aperture for receiving the trocar and having a base portion with two right triangular-shaped sides and a planar anterior surface extending past said base portion depending perpendicular to and between said two right triangular-shaped sides along the hypotenuses of said two right triangular-shaped sides at an angle from the plane of the received trocar;

wherein the user places his fingers above and below said planar anterior surface to securely guide the trocar.

2. The apparatus of claim 1, wherein said stand is metal.

3. A retropubic ligature carrier apparatus for use in actuating an operation through bodily tissues, especially in the treatment of female urinary incontinence, comprising:

a trocar; and a stand, serving as a bridge for said trocar, said stand having an aperture for receiving said trocar and having a base portion with two right triangular-shaped sides and a planar anterior surface extending past said base portion depending perpendicular to and between said two right triangular-shaped sides, along the hypotenuses of said two right triangular-shaped sides at an angle from the plane of said trocar once received in said aperture;

wherein the user places his fingers above and below said planar anterior surface to securely guide said trocar.

4. The apparatus of claim 3, wherein said stand is metal.

5. The apparatus of claim 3, wherein said trocar has a cutting tip.

6. The apparatus of claim 3, wherein said exaggerated planar anterior surface depends at a 20 degree angle from the plane of said trocar.

7. The apparatus of claim 3, wherein said trocar has a spiral tip, resembling screw threads.

8. The apparatus of claim 3, wherein said trocar has an eye.

9. The apparatus of claim 3, wherein said trocar has a striated handle.

* * * * *